United States Patent
Gómez Hernández et al.

(10) Patent No.: US 10,004,235 B2
(45) Date of Patent: Jun. 26, 2018

(54) METHOD FOR THE TREATMENT AND CONTROL OF POST-HARVEST DISEASES IN FRUITS AND VEGETABLES AND COMPOSITIONS COMPRISING NATURAL EXTRACTS AND PLANT-STRENGTHENING AND/OR FUNGICIDAL FORMULATIONS FOR USE IN SAID METHOD

(71) Applicant: DECCO WORLDWIDE POST-HARVEST HOLDINGS B.V., Paterna (Valencia) (ES)

(72) Inventors: Enrique Gómez Hernández, Paterna (ES); Juan José Mascarós Torres, Paterna (ES)

(73) Assignee: DECCO WORLDWIDE POST-HARVEST HOLDINGS B.V., Paterna (Valencia) (ES)

( * ) Notice: Subject to any disclaimer, the term of this patent is extended or adjusted under 35 U.S.C. 154(b) by 379 days.

(21) Appl. No.: 14/768,473

(22) PCT Filed: Jan. 29, 2014

(86) PCT No.: PCT/ES2014/070064
§ 371 (c)(1),
(2) Date: Aug. 18, 2015

(87) PCT Pub. No.: WO2014/128321
PCT Pub. Date: Aug. 28, 2014

(65) Prior Publication Data
US 2016/0000089 A1  Jan. 7, 2016

(30) Foreign Application Priority Data
Feb. 20, 2013  (ES) .................................. 201330227

(51) Int. Cl.
| | | |
|---|---|---|
| *A01N 59/26* | (2006.01) | |
| *A01N 65/00* | (2009.01) | |
| *A01N 65/24* | (2009.01) | |
| *A23L 3/3472* | (2006.01) | |
| *A23B 7/154* | (2006.01) | |
| *A23B 7/157* | (2006.01) | |
| *A01N 35/02* | (2006.01) | |
| *A01N 57/12* | (2006.01) | |

(52) U.S. Cl.
CPC ............. *A01N 59/26* (2013.01); *A01N 35/02* (2013.01); *A01N 57/12* (2013.01); *A01N 65/00* (2013.01); *A01N 65/24* (2013.01); *A23B 7/154* (2013.01); *A23B 7/157* (2013.01); *A23L 3/3472* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 7,465,469 B2 | 12/2008 | Ben-Yehoshua | |
| 2004/0234662 A1* | 11/2004 | Ben-Yehoshua | ....... A01N 27/00 426/532 |
| 2013/0236562 A1* | 9/2013 | Sardo | ..................... A01N 59/26 424/605 |

FOREIGN PATENT DOCUMENTS

| | | |
|---|---|---|
| EP | 2 245 939 | 11/2010 |
| ES | 2 278 052 | 8/2007 |
| ES | 2 387 488 | 9/2012 |
| FR | 2 913 177 | 9/2008 |
| WO | 2012/069576 | 5/2012 |
| WO | WO2012069576 | * 5/2012 |

OTHER PUBLICATIONS

International Search Report dated Mar. 18, 2014 in International Application No. PCT/ES2014/070064.
Second Office Action dated Nov. 14, 2017 in European patent application No. 14753970.4.
Sivakumar et al.: "Control of postharvest diseases of rambutan using cinnamaldehyde". Crop Protection, vol. 21, No. 9, Nov. 1, 2002, pp. 847-852.

* cited by examiner

*Primary Examiner* — Jennifer A Berrios
(74) *Attorney, Agent, or Firm* — Wenderoth, Lind & Ponack, L.L.P.

(57) ABSTRACT

The present invention relates to a method for the control and the treatment of post-harvest diseases in fruits and vegetables by means of simultaneous and combined application of (i) a first formulation, which is aqueous or in the form of an emulsifiable concentrate, which comprises a plant extract and is applied in the form of an aqueous solution and (ii) a second formulation, in the form of an emulsifiable concentrate, soluble liquid or concentrated suspension, which is applied as an aqueous solution, selected from amongst: a plant-strengthening formulation that contains at least one phosphite salt; a fungicidal formulation that contains at least one synthetic fungicide of the phosphonate family, preferably ethyl phosphonic acid salts; or a combination thereof. Each formulation may be a different composition or form part of a single composition. A further subject matter of the present invention is therefore said composition for post-harvest protection of fruits and vegetables which is constituted by the combination of the aforementioned components.

6 Claims, 1 Drawing Sheet

METHOD FOR THE TREATMENT AND CONTROL OF POST-HARVEST DISEASES IN FRUITS AND VEGETABLES AND COMPOSITIONS COMPRISING NATURAL EXTRACTS AND PLANT-STRENGTHENING AND/OR FUNGICIDAL FORMULATIONS FOR USE IN SAID METHOD

FIELD OF THE INVENTION

The present belongs to the field of the chemical industry, more specifically to the area of agricultural chemistry and horticulture, such as the development of compositions and methods for the post-harvest treatment of fruits and vegetables.

PRIOR ART OF THE INVENTION

Fruits and vegetables, in particular citrus fruits, but also apples, pears, peaches, tropical fruits, amongst others, require, after the harvesting thereof, and during the commercialization period (the period known as post-harvest which is the time spent from the harvest until arriving to the end consumer), fungicidal treatments in order to avoid the rotting since the losses produced by said decomposition phenomena would make the commercialization thereof unviable. The existing solution, used for many years is the application of post-harvest fungicidal treatments.

The fungicidal treatments usually applied are based on synthetic chemical products, the most widely used being imazalil, thiabendazole, guazatine and orthophenylphenol amongst others with the object of controlling the instance of decomposition. Given the wide spectrum of diseases which affect crops in post-harvest, above all citrus crops and the difficulty in applying suitable measures, such as the rotation of treatments or the mixture of the same, there is the risk that resistance or low efficacy phenomena of the fungicides arise. If additionally in some markets the commercial pressure of supermarkets is causing the number of treatments (of synthetic fungicides) to be applied to be increasingly limited, such that on many occasions work is only allowed to be carried out with one of them (generally imazalil) which, in addition to not controlling the entire spectrum of diseases, the use thereof in isolation is causing the development of resistances. As if this were not enough, these distribution chains are requiring that the residues of the fungicides, which they authorize, have a residue which is half or one third of that which is permissible. This is causing, in addition to serious phytosanitary problems, a significant disadvantage compared to third party, more distant countries since said countries can treat at the suitable doses, given that the transport time of the fruit allows for the degradation and the reduction of the residue.

In addition to these factors, there is the fact that there are few active materials authorized in post-harvest, therefore the rotation of the treatments is very short and there are more possibilities for the emergence of resistances than in other phytosanitary markets. Furthermore, the condition of "confined environment" of chambers and storage facilitates the exponential development of the same.

Furthermore, the application conditions in closed environments causes there treatments to have many particularities which distinguish them from normal phytosanitary treatments, fundamentally from the point of view of toxicity, but additionally they suffer the exacerbation of problems in that they also have their occurrence in other types of phytosanitary treatments, such as pre-harvest fungicidal treatments in the field such as the problems of resistances i.e. loss of efficacy or loss of sensitivity of the organism object of the control thereof:

due to the use thereof in confined environments, they are more susceptible to the loss of efficacy, which is called the emergence of resistances to the efficacy of fungicides.

due to being a reduced market, there are only a small number of active materials registered, therefore the previous point is a serious problem with no easy solution.

there is significant pressure on the part of the supermarket chains in demanding absence of decay as well as a, sometimes, contradictory pressure to limit to the maximum extent synthetic phytosanitary products to be used in post-harvest (in fruit and vegetable storage facilities). The latter are limiting to the maximum extent the number of applicable active materials and they even limit the residue to a percentage of the value permissible by the regulations. This facilitates the emergence of resistances, incomplete treatments and lack of efficacy.

the fungicides are subjected to significant pollutant pressure which produces problems of low efficacy and emergence of resistances.

The result of all the above is that there are increasingly more problems of decay, emergence of resistances and therefore claims from clients, as well as there being increasingly greater demands in certain markets that the fruits have the lowest possible number of fungicidal residues or are treated with products (such as food additives, plant extracts, products known as GRAS, elicitors, etc.) with the lowest possible environmental and toxicological impact, reducing to a minimum the application of synthetic fungicides.

In this sense, in the past the application of plant extracts by means of applications in aqueous solution or mixed with waxes was presented, which have provided an acceptable level of efficacy in experiments, however, at effective doses they are clearly phytotoxic due to the oxidant properties thereof which damage the skin of the fruits. Specifically, the problems of phytotoxicity produced by the plant extract formulations have stopped or slowed the use of these types of natural products in aqueous application (drencher, bath or spray in line of treatment) due to the high oxidation of the tissues produced by these essential extracts, normally terpenes, aldehydes or phenols. As will be seen in the following section, it has been verified that this oxidant effect can be reduced by the combined application of the plant extract with a reducing agent which in turn can provide systemic efficacy, as is demonstrated in the present invention.

Therefore, together with the previously mentioned problems, the special requirements which the inventions attempts to resolve are:

Minimum use of synthetic fungicides, however, achieving the aims of controlling decay.

Use, if possible, of synthetic fungicides in doses lower than those normally used (one quarter or half of the dose of those specified on the label of the product, preferably being half the dose) for reducing the level of residues but without the emergence of resistances and with the control of decay.

Collaborating in the control and the inhibition of the emergence of resistances to synthetic fungicides which can be used, still in the case where the application doses were lower than those established.

Research the synergetic effect of the combined application of plant-strengtheners and/or elicitors with concentrated emulsifiable formulations of plant extracts which allow the obtained efficacy to be increased and in the same way the emergency of resistances to be avoided.

Research the control of the phytotoxic effect of the plant extract by means of the combined application with plant-strengtheners and/or synthetic fungicides with known reductive character.

In view of the foregoing, the object of this invention is to obtain an alternative method of protection against post-harvest rotting in which use of synthetic fungicides must be low or non-existent, or as a combined treatment to reduce the use of synthetic fungicides or for the control or inhibition of the incidences of resistances in normal treatments. Essentially, the present invention relates to the control of post-harvest diseases in fruits and vegetables with the combined use of compositions with synergetic effects, comprising the combined application of a strengthening formulation (elicitor) based on phosphite salts and/or a synthetic fungicidal formulation of the phosphonate family or the aluminum salts of phosphonic ethyl acid (such as for example phosethyl al) with a principal formulation which is a formulation based on plant extracts. The application of the formulations is carried out in a drencher, bath or spray in a separate or combined manner (in one same composition) in the preparation line of post-harvest treatments of fruits and vegetables, also having achieved a stable composition suitable for those purposes which is composed of the previously cited formulations.

DESCRIPTION OF THE INVENTION

The principal object of this invention is therefore a method for the post-harvest treatment of fruits and/or vegetables which comprises applying simultaneously and in a combined manner:
- a first formulation, which is aqueous or in the form of an emulsifiable concentrate, which comprises at least one plant extract and which is applied in a water solution at a non-phytotoxic concentration, and
- a second formulation in the form of an emulsifiable concentrate, soluble liquid or concentrated suspension and which is applied as an aqueous solution, selected from the group consisting of:
  - a plant-strengthening formulation which contains at least one phosphite salt;
  - a fungicidal formulation which contains at least one synthetic fungicide of the phosphonate family; and
  - a combination of both formulations;

on the fruit and/or vegetables by means of one of the forms selected from the group consisting of drencher, bath and spray.

Within the scope of the present invention, plant extract is understood as the active substances extracted from plants, fruits and vegetables in general and which are always generally essential oils of the aldehyde, terpene or phenol type.

By "non-phytotoxic concentration" it is understood that it is the suitable concentration at which the plant extract can be applied in combination with the rest of the formulations for achieving the proposed objectives, at such concentration of the extract where no significant deterioration of the fruits and/or vegetables on which it is applied can be detected. In turn, "no significant deterioration" is understood as the concentration of the extract equal to or lower than that where no staining or burning of the fruit is produced due to the corrosive effect of the treatment. The suitable dose depends on the plant extract used in the formulation, thus can be greatly varied depending on the composition thereof; thus for example, the dose suitable for a cinnamon extract or any other extract which contains cinnamaldehyde is equal to or less than 1,500 ppm, while for other extracts which contain mainly eugenol, the non-phytotoxic concentration is equal to or less than 500 ppm.

In the prior art, it has been verified that the formulations developed based on plant extracts are of the emulsifiable concentrate type given the physiochemical characteristics of said plant extracts. It is known that natural extracts, given the chemical structure thereof and the predominant chemical group thereof (aldehydes, phenols, terpenes . . . ), have a significant fungicidal capacity. However, this capacity is cancelled by the aggressive phytotoxic character of the extract itself. In this way, an effective dose of plant extracts is phytotoxic and, however, a non-phytotoxic dose is less effective or ineffective.

This is the reason that the isolated application in drencher, bath or spray of a formulation of a high dose of natural extracts (the doses which have been demonstrated to be effective are 5,000 ppm) provides great control of the post-harvest diseases of citrus fruits. However, the oxidant effect due to the chemical nature of the natural extracts causes them to simultaneously produce significant phytotoxicity (see example 1); this effect is observed in all the plant extracts. Therefore, the isolated application of plant extracts does not appear viable, in spite of the efficacy which they have demonstrated in post-harvest treatments.

In the same manner, it has also been verified that lower doses of the plant extracts combined with synthetic fungicides for attempting to increase the efficacy of the product reducing the risks of phytotoxicity also do not avoid risks of phytotoxicity (see example 2). Thus it has been verified that at a dose of more than 1,000 ppm when the plant extract is applied without a reducer (phosphite or phosphonate) and mixed with synthetic fungicides, such as guazatine or prochloraz, it produces phytotoxicity.

However, the combined use by means of drencher, bath or spray of the principal formulation based on plant extracts with other formulations which comprise one or more reducing agents which have elicitor activity (for example phosphite salts) or fungicidal activity (a synthetic fungicide of the phosphonate family, preferably of ethyl phosphonic acid salts) has demonstrated, at suitable treatment doses, which are described further on (preferably between 500 ppm and 1000 ppm), sufficient efficacy (see example 4) and absence of phytotoxicity even in combination with other synthetic fungicides (see example 3).

However, by means of the present invention, it has been set out to solve this problem in various manners. The first was combining the formulation of plant extract at non-phytotoxic concentrations (for example less than 500 ppm for eugenol, less than 1,500 for cinnamon extract, which contains a minimum of 70% cinnamaldehyde) with other natural or elicitor products (plant-strengtheners) such that the synergetic effectiveness reached levels similar to those achieved with problems of phytotoxicity, but without these being produced. The second was the research of products which allowed the problems of phytotoxicity produced by the plant extracts to be reduced. Such problems of phytotoxicity are generally produced by oxidation, given the chemical characteristics of the products used (phenols, aldehydes, terpenes, etc.). It is known that the elicitors of the family of phosphite salts such as potassium phosphite or calcium phosphite together with others, have a susceptibility to oxidize to phosphate, i.e. they have a reductive character. The same occurs with the fungicides of the phosphonate family such as for example ethyl phosphonic acid salts and more specifically phosethyl al. Therefore, this reductive character is very beneficial when it is applied together with natural extract formulations, since the very oxidation thereof reduces the oxidant effect on the skin of the fruits produced by the natural extracts.

Therefore, the object of the invention is the application by means of drencher, bath or spray of formulations comprising natural extracts and formulations with a reductive character. With the combined and simultaneous application a synergetic effect of fungicidal efficacy is achieved in the control of the diseases of fruits and vegetables, together with the reductive effect of the elicitor (phosphite salt) and/or the synthetic fungicide based on phosphonates which reduce the phytotoxic oxidant effect of the plant extracts. The basis of the invention thus consists of the synergy which takes place as a result of the combined application of the components such that they have sufficient fungicidal efficacy, avoiding all the possible problems of phytotoxicity which can be produced due to the plant extract.

It has been seen that the phosphite salts do not only have a plant-strengthening or elicitor effect (facilitate the defenses against fungi of the fruit itself), but that they also, chemically, have a reductive character, i.e. they oxidize, therefore with the oxidation thereof in the presence of oxidants (as is the case of the natural extracts) it can protect the skin of the fruits from the potential phytotoxicity produced by the same, giving a synergetic effect between both components. Similarly, a synthetic fungicide with a very similar chemical structure, the ethyl phosphonic acid salts, also has a reductive character which helped to achieve the absence of any phytotoxic effect by oxidation of the natural extracts in the application thereof. Therefore, the present invention encourages the combined application of the phosphite plant-strengthening salts and/or the fungicidal salts of the phosphonate family for reducing the oxidant effect of the natural extracts. In the same way, said combined action provided a synergetic effect in the control of post-harvest diseases which in the same way helped to reduce the application dose of the natural extracts from 5,000 ppm to less than 1,500 ppm and preferably between 500-1,500 ppm such that the risk of phytotoxicity is reduced further still, providing good efficacy. As will be seen in the examples, this has been demonstrated and forms the basis of the invention.

In a preferred embodiment of the method, the formulations described here can be applied mixed with coatings and waxes commonly applied for these types of edible products. In this case, the formulations mixed with the coatings and waxes are applied by means of spray.

One option of the method consists of combining the previously mentioned formulations in one single composition, such that said composition encompasses the formulation based on plant extract with the fungicidal formulation and/or plant-strengthening formulation. In this case, the method comprises applying one single composition. Consequently, a second object of the present invention is a composition for the control and treatment of post-harvest diseases in fruits and/or vegetables as previously described, that is to say:

a first formulation, which is aqueous or in the form of an emulsifiable concentrated, which comprises at least one plant extract and which is applied in a water solution at a non-phytotoxic concentration, and a second formulation in the form of an emulsifiable concentrate, soluble liquid or concentrated suspension and which is applied as an aqueous solution, selected from the group consisting of:

a plant-strengthening formulation which contains at least one phosphite salt;

a fungicidal formulation which contains at least one synthetic fungicide of the phosphonate family; and a combination of both formulations.

According to the previous description, this alternative means for the control of post-harvest diseases in fruits and vegetables consists, on the one hand, of the combined synergetic treatment of a first component, which is a formulation based on plant extracts with a second component which is a plant-strengthening (elicitor) of the family of phosphite salts. On the other hand, this synergetic treatment can also be the result of the combined application of a composition which comprises the first mentioned component, which contains plant extracts, plus a second component which is a formulation based on a fungicide of the phosphonate family such as for example phosphonic ethyl acid salts. It is also possible to include both, the plant-strengthening formulation and the fungicidal formulation, in the composition together with the component which contains the plant extract, reinforcing the effects of both on the product to be treated and on the extract which accompanies them.

These formulation used in the composition, object of interest, phosphite salts on the one hand and salts of the phosphonate family such as phosphonic ethyl acid offer efficacy in the control of the post-harvest diseases in fruits and/or vegetables, such as citrus fruits, therefore the combined application of formulations of natural extracts with elicitor and/or fungicidal formulations offers a simultaneous solution to both problems, lack of efficacy and phytotoxicity problems One final object of the invention is the use of the composition defined in any of the form and compositions thereof for the treatment of post-harvest diseases in fruits and/or vegetables.

DETAILED DESCRIPTION OF THE INVENTION

When referring to the method of application of the composition described in any of the variants described below for the post-harvest treatment of diseases in fruits and/or vegetables, said application, by means of drencher, bath or spray can be carried out in one or more applications on the pieces to be treated following the harvesting thereof, although in the most preferred case one single application is sufficient. More preferably, the formulations are applied within 48 hours following the harvesting, preferably immediately following the harvesting, with an application time of the formulations of between 30 seconds and 1 minute, the more preferred time being 40 seconds.

In a preferred case of the invention, the first formulation is a concentrated emulsifiable formulation. Also preferably, it contains the plant extract in a percentage by weight of the total of the formulation of between 1 and 50%, 30% being more preferable.

In general, the plant extract can be an extract selected from the group consisting of clove extract, cinnamon extract, citrus extract, garlic extract and other similar vegetables and plants or any combination thereof. Said plant extract, which may be of the family of aldehydes, phenols or terpenes of plant origin is preferably an extract which contains mainly eugenol such as clove extract, although it is more preferably a plant extract which contains cinnamaldehyde (cinnamic aldehyde) such as cinnamon extract. It must be noted here that in spite of the eugenol also being extracted from the leaf of the cinnamon, when, in the present document, cinnamon extract is cited, it should be understood as it is understood in the technical field, that said extract is extracted from the stem of the cinnamon and truly smells of cinnamon due to its high content of cinnamaldehyde which is what provides such odor. The cinnamon extract has as its main component cinnamaldehyde in a concentration greater than 70%.

In effect, in the cinnamon extract the main component is an aldehyde known as cinnamaldehyde used industrially as a perfume and flavoring agent. According to the bibliography, more than 80% of the cinnamon extract is composed of this natural aldehyde, the rest of the components being, in a much minor manner, thymol, eugenol and others. Cinnamaldehyde is the main active ingredient of the cinnamon extract and it is a synthetic product existing in the industry and is used exhaustively in the food industry, the use thereof has great advantages when determining the combination of less synergetic use concentrations with efficacy, without phytotoxicity and without pernicious effects on the fruit (such as for example phytotoxicity production).

Preferably, the first formulation based on plant extracts which is applied in the post-harvest treatment method contains the plant extract in a quantity by weight/volume of the total of the composition equal to or less than 500 ppm of eugenol when it is an extract which contains eugenol as the main component, i.e. more than 60% of the composition of the extract such as clove extract or citrus extract or garlic extract, while said quantity is equal to or less than 1,500 ppm of cinnamaldehyde when it is a plant extract having a composition higher than 70% of cinnamaldehyde, as is in the preferred case of cinnamon extract. In this last case, the plant extract which contains, as its main component cinnamaldehyde, it is present in a proportion of between 500 and 1,500 ppm inclusive, the range 900-1,500 ppm being more preferable. In the most preferred case of all, the formulation contains the plant extract in a specific percentage of 1,000 ppm. It must be taken into account that the quantity of this component can be given both in relation to the quantity of extract as well as in relation to the quantity of the active component which it contains, in this case the cinnamaldehyde since it is known that a quantity of 1,500 ppm of cinnamon extract contains approximately 1,000 ppm of cinnamaldehyde.

The first formulation can comprise in some cases a combination of plant extracts such as the extract which contains cinnamaldehyde as mentioned, thymol, eugenol and menthol amongst others.

The second formulation also preferably contains the active agent, i.e. the plant-strengthening component or the synthetic fungicidal component in a percentage by weight/volume of the composition of between 1,500 and 2,000 ppm inclusive, although when it is a plant-strengthening formulation said percentage by weight is more preferably between 1,600 and 2,000 ppm, more preferably still 1,800 ppm and when it is a formulation based on a synthetic fungicide of the phosphonate family, it is preferably contained in the formulation in a percentage by weight/volume of the composition of between 1,500 and 2,000 ppm inclusive, the range 1,800-2,000 ppm being more preferable and 1,800 being more preferably still. When the second aqueous formulation is formed by both formulations, the plant-strengthening formulation and the fungicidal formulation, then it contains said formulations in the percentages previously indicated for each one of them separately.

The first formulation can also comprise other elements such as surfactants, emulsifiers and solvents. For example, together with the plant extract, the first formulation can contain polysorbates such as polysorbate 80, copolymers such as Pluronic© which is a triblock copolymer of formula HO(CH2CH2O)20(CH2CH(CH3)O)70(CH2CH2O)20H and which has a molecular weight of approximately 5,800 Da; a solvent such as propylene glycol; or other emulsifiers such as polyethylene glycol 400 dioleate.

In a particular embodiment of the invention, the first formulation has the following elements in parts by volume of the total formulation:
Plant extract: 1-50% p/v
Polysorbate 80: 5-20% p/v
Pluronic©: 5-20% p/v
Polyethylene glycol 400 dioleate: 10-50% p/v
Solvent: quantum satis (qs)

The solvent can be selected from the group consisting of water, ethylene glycol and propylene glycol, propylene glycol being more preferable.

The use of polysorbate 80 is apparently selective since the technical literature indicates that it allows penetrability of the plant extract into the tissues which reduces the oxidant effect thereof, and consequently, the phytotoxicity thereof. However, as indicated in the examples, the phytotoxic effect at the effective doses persists in the application thereof in drencher, which is corrected by means of the present invention.

In a more particular embodiment, the first formulation comprises cinnamon extract as plant extract and specifically comprises an equivalent proportion of cinnamaldehyde which said extract contains of between 0.8% and 40% p/v, such that the following specific formulation results:
Cinnamaldehyde: 0.8-40% p/v
Polysorbate 80: 5-20% p/v
Pluronic©: 5-20% p/v
Polyethylene glycol 400 dioleate: 10-50% p/v
Solvent: qs In terms of the plant-strengthening or elicitor formulation, the phosphite salt which it contains is preferably selected from the group consisting of potassium phosphite, calcium phosphite and sodium phosphite and any combination thereof; even though they are mostly preferred the potassium phosphite salt and the calcium phosphite salt.

Said plant-strengthening formulation can also comprise other elements such as surfactants (ionic and non-ionic), pH regulators, water or similar, resulting in a specific formulation such the one that follows:
Phosphite salts: 10-60%
Non-ionic surfactant: 0-10%
PH regulator: 0-10%
Water: qs With respect to the fungicidal formulation, the synthetic fungicidal element of the phosphonate family can be selected from the group consisting of potassium phosphonate, aluminum phosphonate, calcium phosphonate and ethyl phosphonic acid salts. More preferably, it is selected from the ethyl phosphonic acid salts being more preferably still the family of aluminum salts of ethyl phosphonic acid. In the most preferred case of all, the fungicide is phosethyl al (aluminum tri(ethyl phosphonate). Said fungicidal formulation can comprise together with the synthetic fungicide other elements such as ionic and non-ionic surfactants, dispersants, thickeners, solvents and other similar elements. In a specific embodiment, the fungicidal formulation is the following, in parts by volume of the total formulation:
Phosethyl al: 20-50%
Ionic surfactants: 0-10%
Non-ionic surfactants: 0-10%

Dispersants: 0-10%
Thickeners: 0-1%
Solvent: qs

The solvent can be selected from the group consisting of water, ethylene glycol and propylene glycol, propylene glycol being more preferable.

Numerous combination of components of the present invention were studied and it was observed that the greater combination in terms of the desired properties was the combined application of a potassium phosphite formulation as a plant-strengthening or phosethyl al formulation as a fungicidal formulation with a concentrated emulsifying formulation of cinnamon extract, the applications of which on fruits and vegetables presented very good behavior in the control of diseases, with total absence of phytotoxicity at the doses which were synergistically determined as demonstrated in the proposed examples.

Definitively, it has been proven that the combined application of the formulations described per se has sufficient fungicidal properties for being applied in a combined manner while the pressure of the diseases due to fungi and bacteria is not high, in this case substituting completely the use of different synthetic fungicides to those described (of the family of phosphoric ethyl acid salts). Although this criteria, the pressure of the diseases, is a subjective term which depends on the exporter of the product, in the scope of the present specification it is understood as "not very high" since the level of daily rotting detected in the center is lower than the average of annual rotting in the center when a conventional treatment was carried out and is being controlled by the treatment of the invention. Conversely, high disease pressure is understood when the level of rotting determined in the center is greater than the average annual level of rotting of the center when a conventional treatment was applied due to the fact that the fruit has poor condition or due to climatic conditions; given that in the effect of the diseases other factors can affect in addition to the treatment of the invention, it may be that the support with the use of additional synthetic fungicides is made necessary.

Thus in the specific case of high disease pressure it is possible that the fungicidal formulation previously described in any of the variants thereof also includes a second synthetic fungicide commonly used in post-harvest, however, does not belong to the family of ethyl phosphonic acid salts (for example, thiabendazole, imazalil, orthophenylphenol, fludioxonil, pyrimethanil, propiconazol, tebuconazole, quaternary ammonium salts, DDAC, DDACarbonate, guazatine, amongst others). If this second fungicide is added, it must be done at lower or normal usage doses (that is to say, one quarter or half the normal doses indicated on the label of the commercial product), utilizing the synergetic effect of the combination of the coating and slightly increasing the synthetic fungicidal residue. In these cases, in spite of the fact that the risks of phytotoxicity production are very significant, it is possible to fulfil the objectives set out for the present invention thanks to the addition of the plant-strengthener and/or fungicide, preferably in the form of a phosphorous acid salt (such as potassium phosphite) or preferably an ethyl phosphonic acid salt (such as phosethyl al), respectively. As has been said, this susceptibility to phytotoxicity is due to the special characteristics of the plant extracts, generally aldehydes, terpenes and/or phenols, aggressive oxidants of the tissues of the fruit and vegetables, which cause this application to be capable of producing a pernicious phytotoxicity effect which is increased when it is mixed with other synthetic fungicides. However, and as has also been demonstrated, another beneficial effect of the invention, aside from the synergetic activity thereof in the control of diseases, is the reductive character of the plant-strengthener based on phosphoric acid salts (preferably potassium and calcium phosphite), or of the synthetic fungicides based on ethyl phosphonic acid salts (such as phosethyl al), which reduce to a large extent this oxidation effect, since as reducing agents, they prevent the oxidation of the tissues thus they reduce the problem of phytotoxicity due to the application of plant extracts.

As has been mentioned in the previous section, the method for the treatment of post-harvest diseases of fruits and/or vegetables has two principal embodiments: in the first, the formulations are applied by means of drencher, bath or spray in a separated, but simultaneous manner. In the second embodiment, the previously mentioned formulations, in any of the variants thereof, form part of one single composition, that is to say, they are parts or components of a composition developed for the treatment of diseases by means of the described method.

All of the variant of the formulations previously mentioned to define the method are applied to this composition, object of interest, although as it is obvious the formulations are in this case components of the product. Thus, the first formulation is in this case the first component of the composition which contains the vegetables extract in the quantities and percentages previously indicated. The second formulation forms the second component which contains a plant-strengthening formulation, a fungicidal formulation or a combination of both, as has been described.

In one preferred case, the first component which is the first formulation contains the plant extract in a percentage by eight of the total of the formulation of between 1 and 50%, 30% being more preferable. The plant extract can be an extract selected from the group composed of clove extract, cinnamon extract, citrus extract, garlic extract and another similar vegetables and plants or any combination thereof. Said plant extract which can be of the family of aldehydes, phenols or terpenes of vegetable origin is preferably an extract which contains mainly (i.e. more than 70% of) eugenol, such as clove extract, although it is more preferably a plant extract which contains mainly, i.e. more than 70%, cinnamaldehyde (cinnamon aldehyde), such as cinnamon extract.

Preferably, the first component based on plant extracts which is applied in the post-harvest treatment method contains the plant extract in a quantity by weight/volume of the total of the first formulation equal to or less than 500 ppm when it is an extract which contains mainly eugenol, such as clove extract, while said extract is equal to or less than 1,500 ppm when it is a plant extract which contains cinnamaldehyde, such as in the preferred case cinnamon extract. In this last case, the plant extract which contains mainly cinnamaldehyde is present in a proportion of between 500 and 1,500 inclusive, the range 900-1,500 ppm being more preferable. In this most preferred case of all, the formulation contains the plant extract in a specific percentage of 1,000 ppm.

The first component can comprise in some cases, a combination of plant extracts, such as the extract which contains the mentioned cinnamaldehyde, thymol, eugenol and menthol, amongst others.

Also preferably, the second component contains the active agent, i.e. the plant-strengthening component or the synthetic fungicidal component in a percentage by weight/volume of the formulation of between 1,500 and 2,000 ppm inclusive, although when it is a plant-strengthening formulation said percentage by weight is more preferably between 1,600 and 2,000 ppm, 1,800 being more preferable still and when it is a formulation based on a synthetic fungicide of the phosphonate family, it is preferably contained in the formulation in a percentage by weight/volume of the formulation of between 1,500 and 2,000 ppm inclusive, the range 1,800-2,000 ppm being more preferable and 1,800 ppm being more preferably still. When the second aqueous component is formed by both formulation, the plant-strengthening formulation and the fungicidal formulation, then it contains said formulations in the percentages previously indicated for each one of these separately.

The first component can also comprise other elements such as surfactants, emulsifiers and solvents. For example, together with the plant extract, it can contain polysorbates, such as polysorbate 80, copolymers such as Pluronic©, which is a triblock copolymer of formula HO(CH2CH2O)20(CH2CH(CH3)O)70(CH2CH2O)20H and which has a molecular weight of approximately 5,800 Da; a solvent such as propylene glycol; or other emulsifiers such as polyethylene glycol 400 dioleate.

In a particular embodiment of the invention, the first component has the following elements in part by volume of the component total:
Plant extract: 1-50% p/v
Polysorbate 80: 5-20% p/v
Pluronic©: 5-20% p/v
Polyethylene glycol 400 dioleate: 10-50% p/v
Solvent: quantum satis (qs)

The solvent can be selected from the group consisting of water, ethylene glycol and propylene glycol, propylene glycol being more preferable.

In a more particular embodiment, the first component comprises cinnamon extract as plant extract and specifically a proportion equivalent to cinnamaldehyde which contains said extract between 0.8% and 40% p/v, such that the following specific formulation results:
Cinnamaldehyde: 0.8-40% p/v
Polysorbate 80: 5-20% p/v
Pluronic©: 5-20% p/v
Polyethylene glycol 400 dioleate: 10-50% p/v
Solvent: (qs)

In terms of the second component, specifically with respect to the plant-strengthening or elicitor formulation, the phosphite salt which it contains is preferably selected from the group consisting of potassium phosphite, calcium phosphite and sodium phosphite and any combination thereof; although potassium phosphite salt and calcium phosphite salt are preferred above all. Said plant-strengthening formulation can also comprise other elements such as surfactants (ionic and non-ionic), pH regulators, water or similar, resulting in a specific formulation such as the one that follows:
Phosphite or phosphonate salts: 10-60%
Non-ionic surfactants: 0-10%
PH regulator: 0-10%
Water: qs With respect to the fungicidal formulation of the second component, the synthetic fungicidal element of the phosphonate family can be selected from the group consisting of potassium phosphonate, aluminum phosphonate, calcium phosphonate and ethyl phosphonic acid salts. It is more preferably selected from the ethyl phosphonic acid salts, more preferably still from the family of the aluminum salts of ethyl phosphonic acid. In the most preferred case of all, the fungicide is phosethyl al (aluminum tri(ethyl phosphonate). Said formulation can comprise, together with synthetic fungicide, other elements such as ionic and non-ionic surfactants, dispersants, thickeners, solvents and other similar elements. In a specific embodiment, the fungicidal formulation is the following, in parts by volume of the component total:
Phosethyl al: 20-50%
Ionic surfactants: 0-10%
Non-ionic surfactants: 0-10%
Dispersants: 0-10%
Thickeners: 0-1%
Solvent: qs The solvent can be selected from the group consisting of water, ethylene glycol and propylene glycol, propylene glycol being more preferable.

Numerous combinations of components of the present invention were studied and it was observed that the best combination in terms of the desired properties was the combined application of a potassium phosphite formulation as plant-strengthener formulation or of phosethyl al as fungicidal formulation with a concentrated emulsifiable formulation of cinnamon extract, the applications of which on fruits and vegetables showed very good behavior in the control of diseases, with total absence of phytotoxicity at the doses which were determined synergetic as is demonstrated in the proposed examples.

In the specific case of high disease pressure it is possible that the fungicidal formulation previously described in any of the variants thereof also includes a second synthetic fungicide commonly used in post-harvest, however, which does not belong to the family of ethyl phosphonic acid salts (for example, thiabendazole, imazalil, orthophenylphenol, fludioxonil, pyrimethanil, propiconazol, tebuconazole, quaternary ammonium salts, DDAC, DDACarbonate, guazatine, amongst others). If this second fungicide is added, it must be done at lower or normal usage doses (that is to say, one quarter or half the normal dose indicated on the label of the commercial product), utilizing the synergetic effect of the combination of the coating and slightly increasing the synthetic fungicidal residue. In these cases, in spite of the fact that the risks of phytotoxicity production are very significant, it is possible to fulfil the objectives set out for the present invention thanks to the addition of the plant-strengthener and/or fungicide, preferably in the form of a phosphorous acid salt (such as potassium phosphite) or preferably an ethyl phosphonic acid salt (such as phosethyl al), respectively.

EXAMPLES

Figure 1:
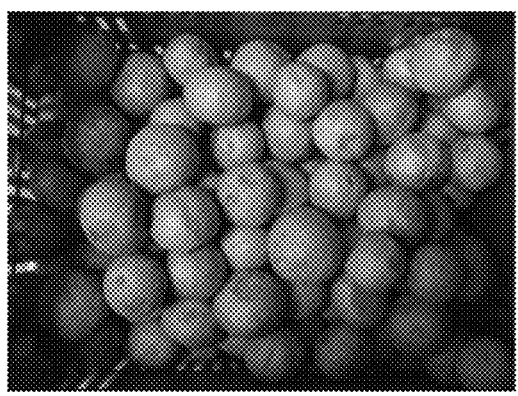
FIG. 1: Photographs which show the existence of severe toxicity produced in the fruit to be applied a composition based only on cinnamaldehyde according to Example 1.
Figure 1:
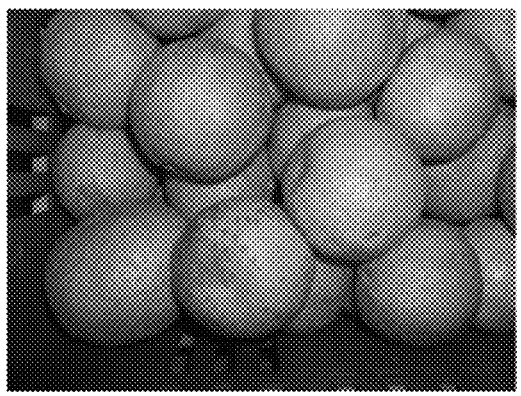

With the aim of providing a better understanding of the invention and according to a practical embodiment of the same, a series of examples accompany this description as an integral part thereof, wherein, in an illustrative and non-limiting character of the invention, the result obtained when applying the following to post-harvest fruits is compared: a post-harvest treatment composition based only on plant extract (Example 1), a composition based on plant extract with conventional synthetic fungicides in normal usage doses (commercial) (Example 2) and compositions according to the present invention (Examples 3 and 4).

Thus, for the selection of the combination of synergetic treatments of plant-strengtheners based on phosphite salts or fungicides of the phosphonate family, specifically ethyl phosphonic acid salts, the efficacy, separately and combined, was studied, as well as the selectivity (presence/absence of phytotoxicity) of the natural extracts, which, given the chemical structure thereof and the predominant chemical group thereof (aldehydes, phenols, terpenes . . . ) has a significant fungicidal capacity, such as extracts of clove, cinnamon, citrus and other vegetables and plants. In all the cases, as has been demonstrated, the fungicidal capacity of the plant extract was cancelled by the aggressive phytotoxic character of the extract itself. Thus, it is demonstrated that in the past formulations were developed for applying by bath, the doses of which had to be modified to avoid problems of phytotoxicity, until the point when said doses are not effective, therefore said applications were not useful and disappeared. It has been effectively proven, for the purposes of this invention, that the use of effective doses are phytotoxic and in addition, the non-phytotoxic doses are, however, not very effective or ineffective. It occurred in the same way as has been explained with the formulation which was developed for the application thereof in drencher, bath or spray in line of application.

Example 1

Test for Determining the Efficacy and Phytotoxicity of a Post-Harvest Treatment Composition Based on 30% Cinnamic Aldehyde at High Doses (1,500 ppm)

The fruit to be treated was Navelina orange and Clemenules mandarin.

The product was applied by means of industrial drencher in the storage centre of the pieces of fruit to be treated with one single post-harvest application over 30 seconds, 24 hours after harvesting. Subsequently, the fruit was introduced into a chamber at ambient temperature for more than one month.

It was proven that all the fruits showed, to a greater or lesser extent, staining and phytotoxicity. As can be observed in Tables 1 and 2, the formulation based on plant extracts used demonstrated, in the application thereof in drencher at the applied doses, the efficacy thereof in the control of the rotting of citrus fruits. However, the phytotoxicity produced makes its commercial use unviable.

TABLE 1

Results of the analysis for the Navelina orange

| Ref. | Treat. | % Rotten | % Efficacy | % Rotten Pen. spp. | % Efficacy |
|---|---|---|---|---|---|
| II | Thiabendazole 60% (3 mL/L) | 2.4 | 82.05 a | 0.9 | 93.83 a |
| III | Cinnamon extract (5 mL/L) | 3.2 | 76.33 a | 2.6 | 79.49 b |
| O | OBSERVER | 14.13 | 0 b | 14.0 | 0 c |

TABLE 2

Results of the analysis for the Clemenules mandarin

| Ref. | Treat. | % Rotten | % Efficacy | % Rotten Pen. spp. | % Efficacy |
|---|---|---|---|---|---|
| II | Thiabendazole 60% (3 mL/L) | 5.63 | 38.69 ab | 2.23 | 69.92 a |
| III | Cinnamon extract (5 mL/L) | 6.0 | 33.2 ab | 1.57 | 76.54 a |
| O | OBSERVER | 9.47 | 0 b | 7.1 | 0 b |

Example 2

Figure 2:
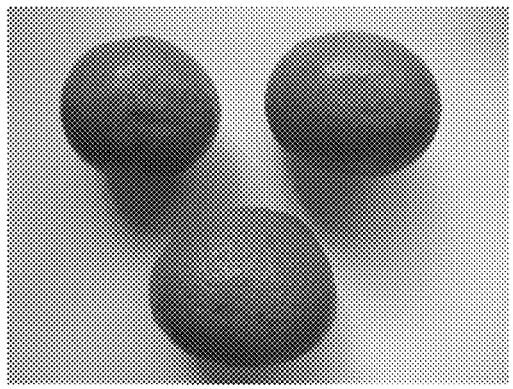
FIG. 2: Photographs which show the phytotoxicity produced in the fruit to be applied a composition based on cinnamaldehyde as plant extract combined with synthetic fungicides according to Example 2.
Figure 2:
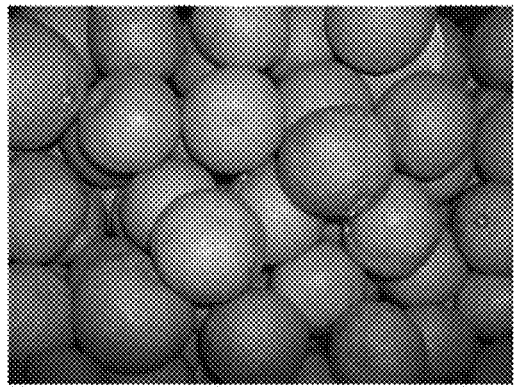

Test for Determining the Efficacy and Phytotoxicity of a Post-Harvest Treatment Composition Based on 30% Cinnamic Aldehyde at Low Doses Combined with Synthetic Fungicides It was proven that all the combinations of the plant extract used on the same classes of fruits as in Example 1 with synthetic fungicides gave problems of phytotoxicity, as is shown in the photographs in FIG. 2.

Example 3

Compositions According to the Present Invention

Below various compositions are described according to that which is described in the present invention, which have been tested on the same classes of fruits as in the previous examples, but unlike in those, they have shown absence of phytotoxicity. The concentration of the active substance used in the post-harvest treatment composition is shown in parentheses:

Plant-strengthening formulation, which contains 50% potassium phosphite at the application doses of 0.3-0.35% (1,500-1,800 ppm of potassium phosphite)+plant extract, which is cinnamon extract (30% cinnamaldehyde) at an application dosis of 0.17%-0.34% (500-1,000 ppm of cinnamaldehyde)

fungicidal formulation, which contains (45%) phosethyl acid at the application dose of 0.33-0.45% (1,500-2,000 ppm of phosethyl al)+plant extract, as has been described for the previous formulation** (500-1,000 ppm of cinnamaldehyde).

Fungicidal formulation, as has been described in the previous formulation (1,500-2,000 ppm of phosethyl al)+plant extract, as has been previously described (500-1,000 ppm of cinnamaldehyde)+20% guazatine at the application dose of 0.5% (1,000 ppm of guazatine)

None of the treatments showed phytotoxicity in oranges, mandarins, satsumas, clementvillas, lemons and clemenules, i.e. a wide sampling of varieties of commercialized citrus fruits.

Example 4

Application of a Post-Harvest Treatment Composition According to the Present Invention Industrial test in citrus fruits storage facility in Murcia with a variety of lemon.

In the process, 20 pallets (approximately 20 tonnes of lemons) were introduced into the degreening chamber without treatment and 20 pallets treated in drencher with 30% cinnamaldehyde at 0.2% (600 ppm cinnamaldehyde) and with 50% potassium phosphite at 0.3% (1,800 ppm).

At 7 days of degreening, the results were as follows:
Control fruit, without treatment: 56% rotten by *Penicillium digitatum*
Treated fruit: 5% rotten by *Penicillium digitatum*
Efficacy of the treatment (Abbott*)=91%
Phytotoxicity number of the treatment: 0%.

Conclusions: the combined treatment of a composition formed by 30% cinnamaldehyde and 50% potassium phosphite in drencher has shown a high efficacy in the control of the rotting of post-harvest lemons, demonstrating the synergetic effect of the treatment. Similarly, the reductive effect of the strengthener has allowed the control of the oxidation of the fruits produced by the plant extract (cinnamaldehyde, also called cinnamic aldehyde), no type of staining of the fruits being produced.

The invention claimed is:

1. A method for the treatment and control of post-harvest diseases in fruits and/or vegetables which comprises applying in a simultaneous and combined manner on the fruits and/or vegetables:
   a. a first formulation in the form of an emulsifiable concentrate which has the following elements in parts by volume of the total of the formulation:
      (i) Cinnamaldehyde: 0.8-40% p/v
      (ii) Polysorbate 80: 5-20% p/v
      (iii) Triblock copolymer of formula

and which has a molecular weight of approximately 5,800 Da: 5-20% p/v
      (iv) Polyethylene glycol 400 dioleate: 10-50% p/v
      (v) Solvent: qs
   and which is applied in a water solution at a non-phytotoxic concentration of the cinnamaldehyde of between 500 ppm and 1,500 ppm; and
   b. a second formulation in the form of an emulsifiable concentrate, soluble liquid or concentrated suspension and which is applied as an aqueous solution, which is:
   (i) a fungicidal formulation which contains phosethyl al as synthetic fungicide; or
   (ii) a combination of said fungicidal formulation with a plant strengthening formulation which contains at least one phosphite salt;
   by means of one of the forms selected from the group consisting of drencher, bath and spray.

2. The method according to claim 1, wherein the formulations are applied once on the fruit and/or vegetable following the harvesting thereof, within 48 hours of the harvesting, with an application time of the formulations of between 30 seconds and 1 minute inclusive.

3. The method according to claim 1, wherein the phosphite salt contained in the plant-strengthening formulation is selected from the group consisting of potassium phosphite, calcium phosphite, sodium phosphite and any combination thereof.

4. The method according to a claim 1, wherein the plant-strengthening formulation has the following composition:
Phosphite salts: 10-60%
Non-ionic surfactant: 0-10%
PH regulator: 0-10%
Water: qs.

5. The method according to claim 1, wherein the fungicidal formulation is the following in parts by volume of the total of the fungicidal formulation:
Phosethyl al: 20-50%
Ionic surfactant: 0-10%
Non-ionic surfactant: 0-10%
Dispersant: 0-10%
Thickeners: 0-10%
Solvent: qs.

6. A composition for carrying out the treatment and control method for post-harvest diseases in fruits and/or vegetables described in claim 1, which comprises:
   a. a first formulation in the form of an emulsifiable concentrate which has the following elements in parts by volume of the total of the formulation:
      (i) Cinnamaldehyde: 0.8-40% p/v
      ii Polysorbate 80: 5-20% p/v
      (iii) Triblock copolymer of formula

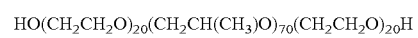

and which has a molecular weight of approximately 5,800 Da: 5-20% p/v
      (iv) Polyethylene glycol 400 dioleate: 10-50% p/v
      (v) Solvent: qs;
   and
   b. a second formulation in the form of an emulsifiable concentrate, soluble liquid or concentrated suspension, which is:
   (i) a fungicidal formulation which contains phosethyl al as synthetic fungicide; or
   (ii) a combination of said fungicidal formulation with a plant strengthening formulation which contains at least one phosphite salt.

* * * * *